United States Patent [19]

Watkins

[11] 4,171,463
[45] Oct. 16, 1979

[54] RODENT PROOF CABLE

[76] Inventor: David Watkins, 9884 Amboy Ave., Arleta, Calif. 91331

[21] Appl. No.: 878,626

[22] Filed: Feb. 17, 1978

[51] Int. Cl.² .................... H01B 7/28; A01N 17/08
[52] U.S. Cl. .................... 174/120 R; 52/517; 106/15.05; 174/136; 405/157; 424/30; 424/153; 428/907
[58] Field of Search ............ 174/110 R, 110 SR, 116, 174/120 R, 120 SR, 121 R, 121 SR, 136; 43/124, 131; 52/101, 517; 106/15 R; 405/157; 424/30, 153; 428/907

[56] References Cited

U.S. PATENT DOCUMENTS

| | | | |
|---|---|---|---|
| 2,222,639 | 11/1940 | Pirk | 174/116 X |
| 2,408,253 | 9/1946 | Diebold | 174/136 |

OTHER PUBLICATIONS

*Modern Drug Encyclopedia and Therapeutic Index,* 13th Edition, edited by Arthur J. Lewis, published by Yorke Medical Books, Dun-Donnelley, New York, 1975, pp. 460-461.

*Primary Examiner*—Laramie E. Askin
*Attorney, Agent, or Firm*—Nilsson, Robbins, Dalgarn, Berliner, Carson & Wurst

[57] ABSTRACT

An electric cable assembly and method for protecting an electric cable assembly for rendering the cable repellent to rodent attacks. A non-lethal toxic chemical, such as lithium chloride, which produces lithium ions when dissolved in the saliva of an animal, is incorporated in an electric cable as either a layer within the electric cable assembly around the circumference and along the length of the cable assembly or by providing a coating on the surface of the electric cable assembly by spraying or painting thereon a mixture containing, for example, lithium chloride. A protective layer or coating may be provided around the layer or coating of the lithium ion producing chemical to protect it against moisture or other environmental conditions.

8 Claims, 3 Drawing Figures

U.S. Patent  Oct. 16, 1979  4,171,463
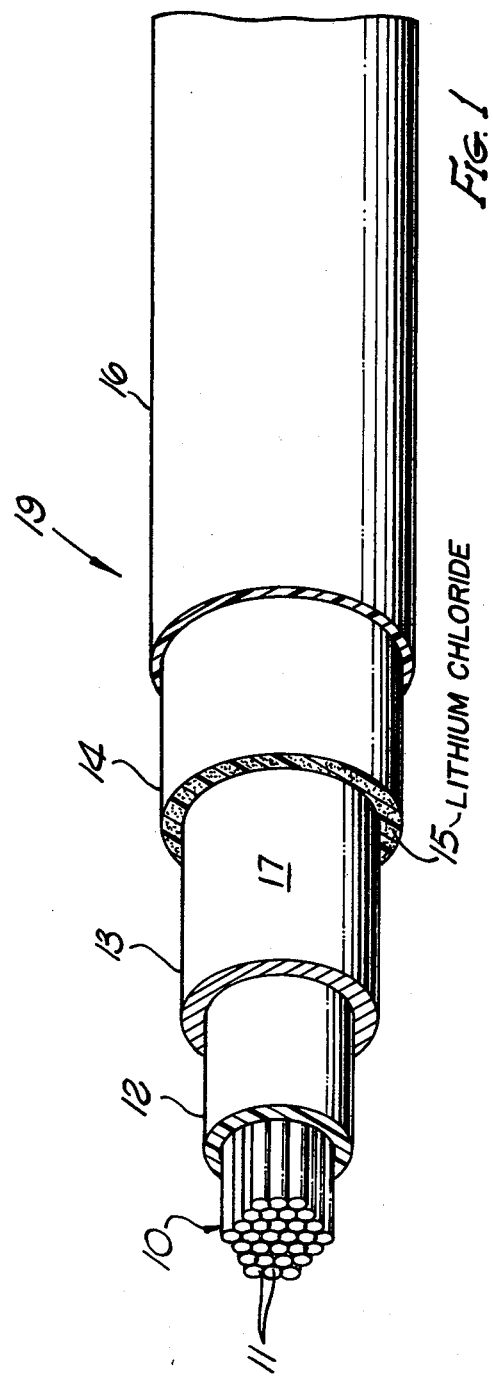
Fig. 1
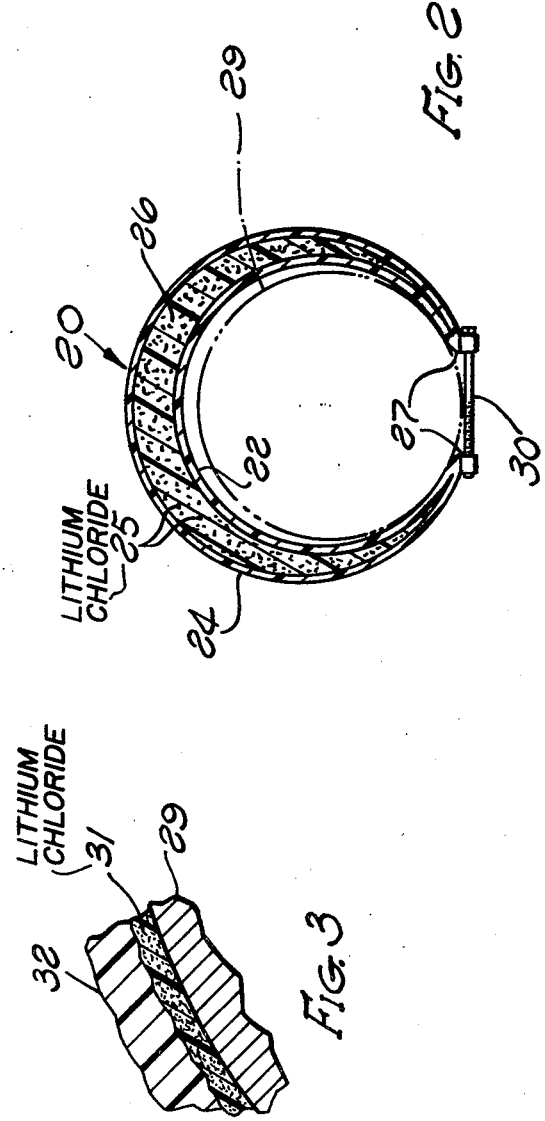
Fig. 2
Fig. 3

RODENT PROOF CABLE

BACKGROUND OF THE INVENTION

The present invention relates to apparatus and methods for rendering electric cables repellent to rodent attacks utilizing the toxic effect of the lithium ion which results when a lithium containing chemical such as the non-lethal toxic chemical agent lithium chloride, is dissolved by the saliva of the rodent.

Many rodents and in particular the fox squirrel (*Sciurus niger*) habitually chew on aerial communication cables. Such chewing frequently causes immediate damage to the cable's wiring or results in damage when rain water or other moisture enters the holes gnawed through the protective outer insulation. In the case of squirrels, chewing on objects which are tough in composition is necessary to prevent their ever-growing incisor teeth from overgrowing. Thus, simply providing a hard outer cable covering is insufficient and may even provide an inducement rather than a deterrent to chewing by squirrels. Because it is frequently undesirable to simply kill the rodents, it is necessary to devise non-lethal apparatus and methods whereby rodents such as squirrels will be prevented or deterred from chewing on cables.

Numerous psychological studies have been performed which show that psychological barriers can be induced by causing an undesirable effect to result immediately after an act is performed. The animal then associates the undesirable result with the immediate preceding act and thereafter changes its behavior to prevent the undesirable result. In the present invention, this knowledge is utilized to incorporate, in a cable assembly, a non-lethal but toxic chemical agent which is capable of causing rapid illness thereby inducing a psychological barrier resulting in a behavioral change opposed to the cable chewing.

The utilization of chemical agents to repel or prevent damage caused by animals either chewing or gnawing on the item sought to be protected is well known. For example, see U.S. Pat. No. 3,426,133, filed Mar. 21, 1966 by James A. Shotton, U.S. Pat. No. 3,269,902, filed Aug. 31, 1964 by Lyle D. Goodhew et al. However, neither of these patents utilize the toxicity of the lithium ion in a non-lethal, toxic chemical such as lithium chloride as an agent to repel rodent attacks on electric cables. In the present invention, however, a layer or surface coating of lithium containing chemical which produces lithium ions when dissolved in the saliva of an animal is provided in an electric cable assembly to provide such a non-lethal but toxic chemical. The lithium ion is the active or illness producing agent and operates to replace the sodium in the sodium-potassium pump of animals thus causing illness (see "Modern Drug Encyclopedia and Therapeutic Index" 13th Edition by Arthur J. Lewis, published by Yorke Medical Books, Dun-Donnelley, New York, 1975, at pages 460–461). Lithium chloride has been found particularly suitable because of the rapidity with which illness is induced upon the ingestion of a minute amount of the chemical. For example, in various experiments test animals became visibly ill within one and a half to five minutes upon the ingestion of as little of 0.3 gram of lithium chloride. The experiments showed that this short time span between ingesting the lithium chloride and becoming sick created an association between chewing on or eating an item and becoming sick. This association caused a behavioral change which later deterred the animals from eating or gnawing on the items which looked like the item onto which the lithium chloride had been applied even though such items did not later contain the lithium chloride. Thus, the present invention is capable of protecting electric cables around which the lithium chloride is placed as well as older cables not so protected but which appear the same to animals such as squirrels.

SUMMARY OF THE INVENTION

A lithium ion producing chemical such as lithium chloride is incorporated to provide a novel electric cable assembly which comprises a cable including the conductive wires and necessary insulation layers. A region is then provided around at least a portion of the circumference of the cable. This region contains a lithium ion producing chemical agent such as lithium chloride (hereinafter reference to lithium chloride is by way of example and is meant to include all non-lethal toxic chemicals which produce lithium ions when dissolved in saliva) or may contain a mixture of a substance which is non-reactive with lithium chloride and lithium chloride. A means is then preferably provided to protect the lithium chloride layer from the environment and particularly from moisture since lithium chloride is water soluble. This means for protecting the region containing the lithium chloride may be an additional insulating region surrounding the cable and may, for example, be polyethylene. The substance into which the lithium chloride may be mixed to provide the protective layer around the cable may be a jelly-like substance or a grease. In actual practice, the regions into which the lithium chloride or lithium chloride mixture is placed is defined by the outside surface of the inside cable and the inside surface of the outer protective layer. In addition, it is preferable that the outside protective layer be relatively thin and penetrable allowing the rodents to chew through and thereby ingest some lithium chloride. By contrast, the inner insulating region surrounding the central wiring region should be substantially stronger and substantially impenetrable to the initial biting by the rodents.

In another embodiment of the present invention, a sheath assembly is provided which fits snugly around the cable and which may be attached to the cable after the cable is in place. The sheath preferably has a relatively thick and strong inside layer for placement adjoining the outside surface of the cable and a second outside layer of relatively thin material to allow penetration by a rodent gnawing on the outside layer. The underside layer and the outside layer are then connected in such a way as to define an inner cavity between the outside layer and the underside layer into which may be placed either pure lithium chloride or a mixture of lithium chloride and a non-reactive binder or other substance.

In still another embodiment of the present invention, a liquid mixture of lithium chloride is prepared utilizing either water or a water-base glue substance. The mixture may then be either sprayed or painted on the surface of an electric cable. The electric cable is then preferably provided with a non-reactive protective coating around the lithium chloride coating to protect the lithium chloride coating from the environment and in particular moisture in the environment. The outside protective coating may be a water-insoluble substance such as an organic epoxy resin or other well known water-insoluble substance.

BRIEF DESCRIPTION OF THE DRAWINGS

These and other advantages and features of the invention will be more apparent from the detailed description below taken in conjunction with the accompanying drawings wherein like reference characters refer to like parts throughout and in which:

FIG. 1 is a cross section of a cable illustrating the electric cable assembly of the present invention;

FIG. 2 is a cross section illustrating a sheath incorporating a layer of lithium chloride and adapted to be placed around an electric cable; and FIG. 3 is a cross section illustrating the resultant cable when the lithium chloride is sprayed or painted on the cable's surface.

DETAILED DESCRIPTION OF THE PREFERRED EMBODIMENT

A behavioral characteristic in many rodents and other animals and in particular the fox squirrel, is the need to chew on objects which are tough in composition to prevent their ever-growing incisor teeth from overgrowing. In order to satisfy the desire to chew and thus prevent the overgrowth of incisor teeth, squirrels and other rodents frequently attack aerial communication cables causing damage necessitating frequent and expensive repairs.

In the present invention, the chemical agent lithium chloride is utilized in novel electric cable assemblies to provide protection against damage caused by the chewing of rodents. Lithium chloride is a particularly suitable agent for this purpose because it has been found that while non-lethal, it is sufficiently toxic, even when ingested in small quantities, to cause immediate illness in animals. In addition to immediately stopping rodents from chewing, the illness induces a psychological barrier in the rodents resulting in a behavioral change opposed to cable chewing.

Referring now to FIG. 1, an electric cable assembly incorporating the present invention is illustrated and includes a central wiring region 10 including a plurality of individual insulated electric wires 11. Surrounding the central wiring region 10 is an inner insulating region 45 which may, for example, incorporate a plastic inner layer 12 immediately surrounding the central wiring region and a liner 13 surrounding the plastic inner layer 12. The insulating region may also include a third layer of insulating material such as polyethylene or other suitable material well known in the art. Adjacent to the outermost layer of the inner insulating region another layer 14 is disposed around at least a portion of the circumference of the cable. This layer 14 is comprised of lithium chloride particles or crystals 15 either alone or in combination with a non-reactive binding substance to aid in affixing the lithium chloride particles or crystals 15 to the surface 17 of the outermost layer of the inner insulating region.

The binding substance may be grease or any other jelly-like substance such as the substance utilized in the unsoldered mechanical unsoldered steel polyethylene jacket cable currently in use by the Bell System or any other suitable material into which lithium chloride particles or crystals may be non-reactively mixed and thereafter affixed to the outermost surface 17 of the inner insulating region of the cable 19. In practice, the binding substance will be such that the lithium chloride particles or crystals will not dissolve and additionally will be protected from moisture. In short, the lithium chloride should not react with the binding substance thereby retaining the toxic quality of lithium chloride.

Surrounding the lithium chloride or lithium chloride mixture layer 14 is an outer insulating region or layer 16 which may for example, also be made of polyethylene or any other suitable material well known in the art. In practice it is preferable that the outer layer 16 be relatively thin to allow the rodent to puncture the outer layer 16 and come in contact with the lithium chloride particles 15.

Although the outer layer will thus be damaged to a certain extent by the initial chewing by the squirrel, such damage will have no significant affect on the cable since the outer layer 16 is primarily for the purpose of holding the lithium chloride layer 14 in place and protecting it from the elements. Furthermore, the outer layer will continue to protect the lithium chloride in the now chewed region with only the exposed lithium chloride in the immediate vicinity of the puncture affected by the elements, particularly if a moisture repellant jelly binder is used in the layer 14 as previously discussed. Because the lithium chloride causes almost immediate illness when it enters the rodent's saliva, only minor inconsequential damage to the outer layer 16 will be done before the rodent will cease chewing because of illness. After one or two such encounters resulting in illness, a psychological barrier will be induced preventing further attacks. In addition, because the rodents will not be able to tell a protected cable from an unprotected one, the rodents induced to avoid the protected cable will also avoid unprotected cables. Because the rodents or squirrels will initially chew the treated cable causing minor damage to the outer layer 16, it is preferable that the liner 13 of the cable 19 be made of a strong material such as steel so that the inner insulating region is relatively impermeable to the initial chewing by the rodents.

It will of course be appreciated that the cable assembly illustrated in FIG. 1 may be obtained utilizing existing cables where the liner 13 of the inner insulating region of the cable assembly of FIG. 1 is the same as the outside insulating region or layer of the existing cable. Thus, the lithium chloride mixture layer 14 may be disposed around this outside surface and a new outside protective layer 16 disposed around the lithium chloride layer 14.

The present invention may also be practiced in a second embodiment illustrated in FIG. 2 wherein a sheath 20 is provided to be affixed around a cable 29. The sheath 20 has an underside layer 22 which is positioned to adjoin the outer surface of the cable 29 when the sheath 20 is in place. The sheath 20 also has an outer layer 24 which may be joined to the underside layer at end points 27 along the length of the sheath by either heating the layers 24 and 22 to cause the end points to be melted together or any other suitable technique. The underside layer 22 and the outside layer 24 of the sheath 20 then define an enclosed region 26 into which may be placed a mixture which includes at least the lithium chloride crystals 25. As in the previous embodiment, lithium chloride particles or crystals alone may be placed in the region 26 or the lithium chloride particles 25 may be first mixed with a water-insoluble jelly-like substance such as grease. Because the rodent must initially chew on the sheath in order to ingest the lithium chloride and become ill, it is preferable that the outer layer 24 of the sheath 20 be of a relatively thin and easily penetrable material. In addition, it is preferable to provide a relatively thick underside layer 22 to prevent rodent penetration when the rodent initially chews on the outside layer 24. In practice the sheath 20 could be made of a preformed resilient plastic material which could be attached to the cable 29 by holding the ends 27 apart to fit the sheath around the cable and then releasing the ends whereupon the sheath would return to its normal shape with the ends 27 close together and the sheath thereby held to the cable without anything more. However, snaps, glue, clips, ties or any other technique or device could also be used as illustrated by the use of a clip 30 in FIG. 2.

A third embodiment of the present invention illustrated in FIG. 3 whereby lithium chloride is utilized to protect cables against damage by extensive rodent chewing, may be provided by formulating a liquid mixture or compound of lithium chloride. This compound or mixture may then be brushed or sprayed on the outer surface of an electric cable 29 as a first layer 31. Because lithium chloride is water soluble it is preferable to then spray or brush on a water-proof sealant such as organic epoxy resin composition or any other suitable water-proof sealant well known in the art as a second coating or layer 32. In practice, the initial lithium chloride layer 31 which is obtained by spraying or brushing a lithium chloride liquid onto the cable, may simply be lithium chloride dissolved in water or may be a common water-soluble glue mixture such as Elmer's Glue.

While the present invention has been described in various specific embodiments and structures in the foregoing specification, it will be appreciated that various details have been incorporated for illustrative purposes only and that such details may be varied widely without departing from the spirit of the present invention.

I claim:

1. An electric cable assembly comprising:
   a cable;
   a region around at least a portion of the circumference of said cable, said region having at least a lithium ion producing chemical disposed therein; and
   means for protecting said lithium ion producing chemical from the environment.

2. The electric cable assembly of claim 1 wherein said lithium ion producing chemical is lithium chloride.

3. An electric cable assembly comprising:
   a central wiring region;
   an inner insulating region surrounding said central wiring region;
   a layer containing at least a lithium ion producing chemical disposed along the length of said inner insulating region and around at least a portion of the circumference thereof; and
   an outer insulating region for defining the outermost surface of said electric cable assembly.

4. The electric cable assembly of claim 3 wherein said layer comprises a mixture including said lithium ion producing chemical and at least one other substance, said other substance being non-reactive with said lithium ion producing chemical.

5. The electric cable assembly of claim 4 wherein said other substance is grease.

6. The electric cable assembly of claim 3 wherein said lithium ion producing chemical is lithium chloride.

7. A sheath apparatus for protecting an electric cable assembly from rodents, comprising:
   a sheath having an enclosed central cavity and having a shape adapted to fit around said electric cable assembly; and
   a mixture including at least a lithium ion producing chemical disposed in said enclosed central cavity.

8. The sheath apparatus of claim 7 wherein said sheath comprises an outside layer and an inside layer adapted to be positioned next to said electrical cable assembly and joined to said outside layer to define said enclosed central cavity, said outside layer being relatively thin and easily penetrated by said rodents and said inside layer being relatively thick and impenetrable by said rodents.

* * * * *